(12) United States Patent
Fini et al.

(10) Patent No.: US 7,278,428 B2
(45) Date of Patent: *Oct. 9, 2007

(54) FACE OR NOSE MASK FOR NON-INVASIVE VENTILATION OF PATIENTS IN GENERAL

(75) Inventors: Massimo Fini, Mirandola (IT); Paolo Bergamaschi, Concordia (IT); Stefano Nava, Crema (IT)

(73) Assignee: Mallinckrodt, Inc., Hazelwood, MO (US)

(*) Notice: Subject to any disclaimer, the term of this patent is extended or adjusted under 35 U.S.C. 154(b) by 78 days.

This patent is subject to a terminal disclaimer.

(21) Appl. No.: 10/998,437

(22) Filed: Nov. 29, 2004

(65) Prior Publication Data

US 2005/0092327 A1   May 5, 2005

Related U.S. Application Data

(62) Division of application No. 10/018,899, filed as application No. PCT/US00/06164 on Mar. 9, 2000, now Pat. No. 6,834,650.

(30) Foreign Application Priority Data

Mar. 12, 1999   (IT)  ............... MI99A0521

(51) Int. Cl.
A62B 18/08   (2006.01)

(52) U.S. Cl. ............ 128/206.26; 128/206.24; 128/205.25

(58) Field of Classification Search ......... 128/206.23, 128/206.24, 206.26, 205.25, 202.28, 202.29, 128/203.11
See application file for complete search history.

(56) References Cited

U.S. PATENT DOCUMENTS

| 2,047,216 | A | 7/1936 | McKesson |
| 2,749,910 | A | 6/1956 | Faulconer, Jr. |
| 2,875,757 | A | 3/1959 | Galleher, Jr. |
| 3,330,273 | A | 7/1967 | Bennett |
| 3,330,274 | A | 7/1967 | Bennett |
| 4,799,477 | A | 1/1989 | Lewis |
| 4,971,051 | A | 11/1990 | Toffolon |
| 5,560,354 | A | 10/1996 | Berthon-Jones et al. |
| 5,660,174 | A | 8/1997 | Jacobelli |
| 5,738,094 | A * | 4/1998 | Hoftman ............... 128/206.26 |
| 6,834,650 | B1 * | 12/2004 | Fini et al. ............. 128/206.26 |

* cited by examiner

Primary Examiner—Justine R. Yu
Assistant Examiner—Shumaya B. Ali
(74) Attorney, Agent, or Firm—Baker Botts L.L.P.

(57) ABSTRACT

The face or nose mask (1) includes a mask body (2) with an inlet (3). The mask body (2) includes a sealing element with a first chamber (10), and a second chamber (11) which can be connected by connectors (12, 13) to a source of pressurized air.

20 Claims, 1 Drawing Sheet

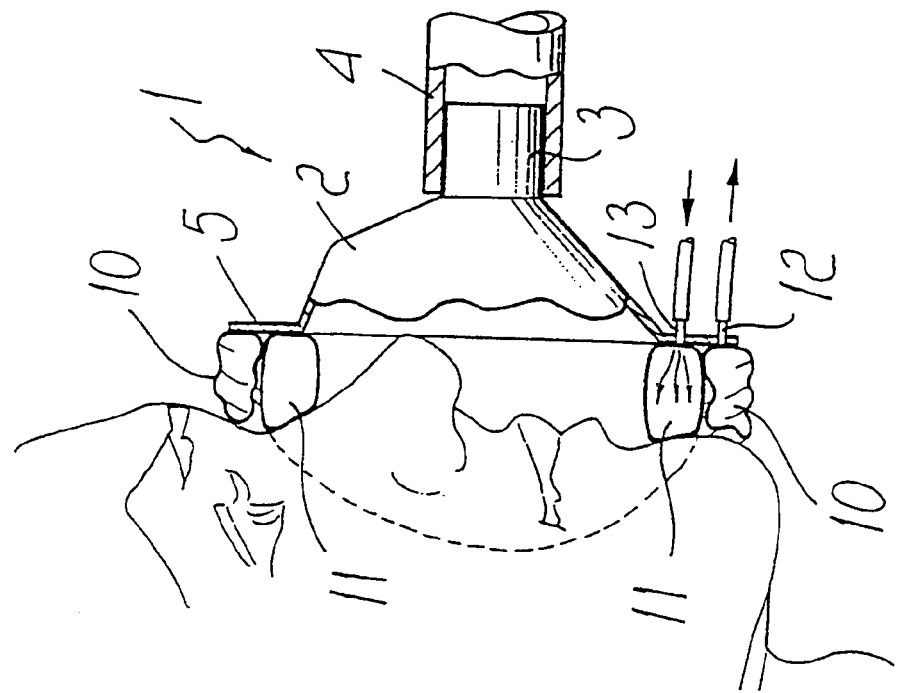
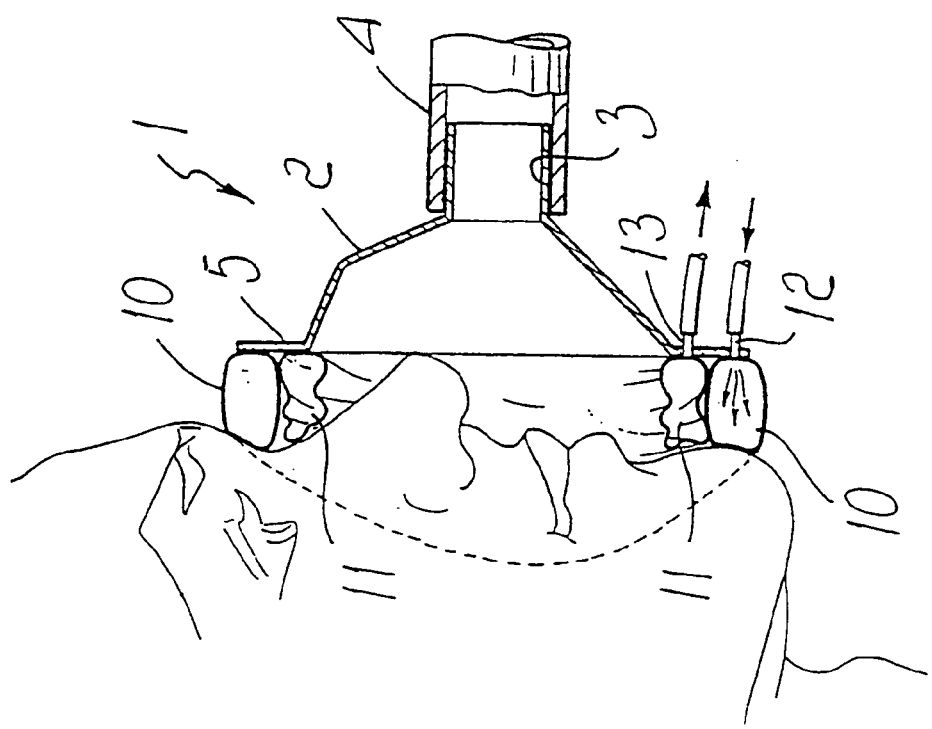

FACE OR NOSE MASK FOR NON-INVASIVE VENTILATION OF PATIENTS IN GENERAL

This application is a divisional of Ser. No. 10/018,899, filed Jun. 6, 2002 now U.S. Pat. No. 6,834,650, which is a national phase of PCT/US00/06164, filed 9 Mar. 2000, claiming priority from Italian Application No. MI 99A000521, filed Mar. 12, 1999.

The present invention relates to a face or nose mask for non-invasive ventilation of patients in general.

It is known that the main problem in long-term ventilation performed by means of a mask is the tolerability of the mask by the patient.

One of the most unpleasant and harmful effects arises from the compression of the skin that is produced by the sealing element provided in the perimetric region of the mask, which is pressed against the user's face; this effect is particularly damaging at the upper nasal region.

The pressure applied by the mask in fact reduces blood flow in the affected part of the skin and in the long term causes pain and sores may form in the region.

In order to try to at least partially solve this problem, masks have already been provided in which the sealing element is formed in practice by an air-filled chamber or air cushion which, in order to reduce the period of contact with the skin, is in practice deflated at least at the upper part of the nasal septum during expiration, a step in which there is no need to provide a seal since the patient is expelling air. The chamber is then instantly reinflated during inspiration, thus forming a seal again and in practice reducing the time of contact between the skin and the inflatable chamber.

Also this solution has not proved to be particularly effective, since the inflation and deflation rate is closely dependent on the ratio between the expiration phase and the inspiration phase and because a relatively high residual pressure always remains and is applied by the mask to the skin.

The aim of the present invention is to eliminate the above-noted drawbacks, by providing a face or nose mask for non-invasive ventilation of patients in general which allows to reduce the time for which the pressure produced by the sealing element of the mask is applied, so that the above-mentioned problems do not occur since blood flow in the affected skin portion is possible at all times.

Within the scope of this aim, a particular object of the present invention is to provide a face or nose mask in which the perfect seal of the mask with respect to the outside is ensured at all times but the region where pressure is applied to the skin changes continuously.

Another object of the present invention is to provide a mask in which the system for inflating the sealing element is independent of the ventilation system, consequently allowing a wide range of adjustment for the pressure values used.

Another object of the present invention is to provide a mask which, by way of its particular constructive characteristics, is capable of giving the greatest assurances of reliability and safety in use.

Another object of the present invention is to provide a face or nose mask for non-invasive ventilation of patients in general which can be easily obtained starting from commonly commercially available elements and materials and is also competitive from a purely economical point of view.

This aim, these objects and others which will become apparent hereinafter are achieved by a face or nose mask for non-invasive ventilation of patients in general, according to the invention, which comprises a mask body provided with an inlet for connection to a ventilation apparatus and perimetrically provided with a sealing element for application to the face of a patient, characterized in that said sealing element comprises at least one first chamber and at least one second chamber which can be connected separately to a source of pressurized air.

Further characteristics and advantages of the present invention will become apparent from the following detailed description of a preferred but not exclusive embodiment of a face or nose mask for non-invasive ventilation of patients in general, illustrated only by way of non-limitative example in the accompanying drawings, wherein:

FIG. 1 is a partially sectional schematic view of the mask according to the invention with the seal provided by one chamber; and FIG. 2 is a view of the mask with the seal produced by the other chamber.

With reference to the above figures, the face or nose mask for non-invasive ventilation of patients in general, according to the invention, generally designated by the reference numeral 1, comprises a mask body 2 which has the conventional configuration of a face or nose mask and is provided with an inlet 3 for connection, by means of a hose 4, to a ventilation apparatus.

In the perimetric region, the mask has a flange 5 at which the sealing element for application to the face of the patient is provided.

The particularity of the invention is constituted by the fact that the sealing element is provided by at least one first chamber 10 and by at least one second chamber 11 which are advantageously arranged side by side, the first chamber being arranged outside with respect to the second chamber.

The chambers have separate connections to a source of pressurized air, and in particular there is provided a first connector 12 for the first chamber 10 and a second connector 13 for the second chamber 11; such connectors are connected to an inflation device which is constituted for example by extremely compact micropumps which can be actuated sequentially so as to release the pressure in one chamber and inflate the other chamber, thus ensuring the seal.

The inflation and deflation rate can be adjusted in any manner, since it is independent of the ventilator of the ventilation system.

In practice it is possible to alternate inflation and deflation with a period of a few seconds, consequently having the advantage that the skin is affected in the same region for a period which is substantially halved, but most of all with the advantage that in practice blood flow is never interrupted or hindered, thus preventing the occurrence of pain and dangerous sores.

In practice, the system adopted consists in removing pressure from one chamber and simultaneously restoring pressure in the other chamber, so that the seal is ensured at all times but the region where pressure is applied to the skin changes.

Advantageously, the chambers have a closed perimeter, but from the conceptual point of view there is no difference if the chambers 10, 11 affect only portions of the face and in any case the regions that are more severely affected by pain or sores, depending on the pressure applied in order to provide the seal.

From the above description it is thus evident that the invention achieves the intended aim and objects, and in particular the fact is stressed that a face mask is provided which has an inflatable sealing element which is entirely autonomous and independent of the ventilator used for ventilation, thus allowing to adjust the pressure inside the individual chambers independently of each other and to provide alternating deflation and inflation of the chambers at a rate which can be adjusted at will in view of the fact that the chambers are separately connected to a source of pressurized air, for example constituted by micropumps.

The invention thus conceived is susceptible of numerous modifications and variations, all of which are within the scope of the inventive concept.

All the details may also be replaced with other technically equivalent elements.

In practice, the materials employed, as well as the contingent shapes and the dimensions, may be any according to requirements.

The invention claimed is:

1. A method for sealing a face or nose mask for non-invasive ventilation of a subject, comprising the steps of:
    providing a mask body having an inlet for connection to a ventilation apparatus and including a perimetric sealing element for application to a subject's face, said sealing element including a first chamber and a second chamber, said first chamber having a first connector connectable to a source of pressurized air, and said second chamber having a second connector connectable to the source of pressurized air, said second chamber being located generally within a perimeter of said first chamber; and
    alternately inflating said first chamber while pressure in said second chamber is released, and inflating said second chamber while pressure in said first chamber is released.

2. A method according to claim 1, wherein:
    said first chamber of said sealing element is an enclosed chamber; and
    said second chamber of said sealing element is an enclosed chamber.

3. A method according to claim 1, wherein alternatively inflating said first and second chambers comprises using the source of pressurized air for inflating said first chamber through said first connector and for inflating said second chamber through said second connector.

4. A method according to claim 3, further comprising supplying gas to at least one breathing passage of the subject through the inlet.

5. A method according to claim 4, wherein each of said first and second connectors is distinct from the inlet.

6. A method according to claim 4, further comprising alternatively inflating said first and second chambers independent from supplying gas to the subject through the inlet.

7. A method according to claim 1, wherein each of said first and second chambers is configured to be positioned around both the nose and mouth of the subject.

8. A mask for ventilating a subject, comprising:
    a mask body having an inlet for connection to a ventilation apparatus for supplying gas to a subject;
    a sealing apparatus coupled to the mask body and configured to be positioned against the subject's face, the sealing apparatus including a first chamber and a second chamber, the second chamber located generally within a perimeter of the first chamber;
    a first connector coupled to the first chamber and operable to communicate with the first chamber to inflate and deflate the first chamber; and
    a second connector coupled to the second chamber and operable to communicate with the second chamber to inflate and deflate the second chamber;
    wherein the first and second chambers are alternately inflatable.

9. A mask according to claim 8, wherein the first and second chambers are configured for at least partial inflation of the first chamber during at least partial deflation of the second chamber and for at least partial inflation of the second chamber during at least partial deflation of the first chamber.

10. A mask according to claim 8, wherein:
    the first chamber of the sealing apparatus is an enclosed chamber; and
    the second chamber of the sealing apparatus is an enclosed chamber.

11. A mask according to claim 8, wherein:
    the first connector is configured for communication with a first pump for inflating the first chamber; and
    the second connector is configured for communication with a second pump for inflating the second chamber.

12. A mask according to claim 8, wherein each of the first and second connectors is distinct from the inlet.

13. A mask according to claim 8, wherein each of the first and second chambers is configured to be positioned around both the nose and mouth of the subject.

14. A mask according to claim 8, further comprising a flange associated with the mask body, wherein both of the first and second chambers are coupled to the flange.

15. A sealing apparatus for a breathing mask, comprising:
    a first chamber having a perimeter, the first chamber inflatable for providing a seal against a subject's face in a first state of the sealing apparatus;
    a second chamber located generally within the perimeter of the first chamber, the second chamber inflatable for providing a seal against a subject's face in a second state of the sealing apparatus;
    a first connector coupled to the first chamber and operable to communicate with the first chamber to inflate and deflate the first chamber; and
    a second connector coupled to the second chamber and operable to communicate with the second chamber to inflate and deflate the second chamber.

16. A sealing apparatus according to claim 15, wherein the first and second chambers are alternately inflatable.

17. A sealing apparatus according to claim 15, wherein the first and second chambers are configured for at least partial inflation of the first chamber during at least partial deflation of the second chamber and for at least partial inflation of the second chamber during at least partial deflation of the first chamber.

18. A sealing apparatus according to claim 15, wherein:
    the first chamber is an enclosed chamber; and
    the second chamber is an enclosed chamber.

19. A sealing apparatus according to claim 15, wherein:
    the first connector is configured for communication with a first pump for inflating the first chamber; and
    the second connector is configured for communication with a second pump for inflating the second chamber.

20. A sealing apparatus according to claim 15, wherein each of the first and second chambers is configured to be positioned around both the nose and mouth of the subject.

* * * * *

UNITED STATES PATENT AND TRADEMARK OFFICE
CERTIFICATE OF CORRECTION

PATENT NO. : 7,278,428 B2
APPLICATION NO. : 10/998437
DATED : October 9, 2007
INVENTOR(S) : Fini et al.

It is certified that error appears in the above-identified patent and that said Letters Patent is hereby corrected as shown below:

Title page, [62]. Please delete the entire paragraph and replace with --Divisional of Application No. 10/018,899, filed Jun. 6, 2002, now Pat. No. 6,834,650, which is a national phase of PCT/US00/06164, filed Mar. 9, 2000.--

Signed and Sealed this

Eighteenth Day of March, 2008

JON W. DUDAS
*Director of the United States Patent and Trademark Office*